United States Patent
Tracy et al.

(10) Patent No.: US 11,447,799 B2
(45) Date of Patent: Sep. 20, 2022

(54) AQUEOUS FERMENTATION FEEDSTOCK AND A METHOD FOR THE PRODUCTION THEREOF

(71) Applicant: SUPERBREWED FOOD INC., New Castle, DE (US)

(72) Inventors: Bryan P. Tracy, Wilmington, DE (US); John Randall Phillips, Middletown, DE (US); Daniel Knox Mitchell, Wilmington, DE (US)

(73) Assignee: SUPERBREWED FOOD INC., New Castle, DE (US)

( * ) Notice: Subject to any disclaimer, the term of this patent is extended or adjusted under 35 U.S.C. 154(b) by 0 days.

(21) Appl. No.: 17/016,480

(22) Filed: Sep. 10, 2020

(65) Prior Publication Data

US 2020/0407760 A1 Dec. 31, 2020

Related U.S. Application Data

(63) Continuation-in-part of application No. PCT/US2019/021643, filed on Mar. 11, 2019.

(60) Provisional application No. 62/641,597, filed on Mar. 12, 2018.

(51) Int. Cl.
*C12P 7/14* (2006.01)
*C12N 9/34* (2006.01)
*C12P 19/04* (2006.01)

(52) U.S. Cl.
CPC ............. *C12P 7/14* (2013.01); *C12N 9/2428* (2013.01); *C12P 19/04* (2013.01); *C12Y 302/01001* (2013.01); *C12Y 302/01003* (2013.01)

(58) Field of Classification Search
CPC ............ C12N 9/2411; C12N 9/2428; C12Y 302/01001; C12Y 302/01003; C12P 21/00; C12P 19/02; C12P 7/06; C12P 19/04; C12P 7/14; Y02E 50/10
See application file for complete search history.

(56) References Cited

U.S. PATENT DOCUMENTS

2014/0106419 A1* 4/2014 Bazzana ............... C12P 7/16
  435/134
2014/0315259 A1 10/2014 Woods et al.
2016/0201152 A1* 7/2016 Medoff .................. C12P 19/02
  127/55

FOREIGN PATENT DOCUMENTS

WO 2017120170 A1 7/2017

OTHER PUBLICATIONS

Lin et al., Ethanol production by simultaneous saccharification and fermentation in rotary drum reactor using thermotolerant Kluveromyces marxianus. Appl. Energy., 2013, vol. 105: 389-394. (Year: 2013).*
Mathews et al., A conceptual lignocellulosic 'feed+fuel' biorefinery and its application to the linked biofuel and cattle raising industries in Brazil. Energy Policy, 2011, vol. 39: 4932-4938. (Year: 2011).*
Schwartz et al., From Fields to Fuels: A Student Workshop on Conversion of Biomass to Ethanol. ASABE Meeting Presentation, Paper No. 1008874, 2010, 9 pages. (Year: 2010).*
Yucel et al., Ethanol fermentation characteristics of *Pichia stipitis* yeast from sugar beet pulp hydrolysate: Use of new detoxification methods. Fuel, 2015, vol. 158: 793-799. (Year: 2015).*
Elliot et al., Biorefinery Concept Development Based on Wheat Flour Milling. Pacific Northwest National Laboratory is operated by Battelle for the U.S. Department of Energy under Contract DE-AC06-76RL0 1830, Jan. 2002, pp. 1-24. (Year: 2002).*
Wu et al., Mechanochemical effects of micronization on enzymatic hydrolysis of corn flour. Carbohydrate Polymers, 2008, vol. 72: 398-402. (Year: 2008).*
Written Opinion of the ISA for priority application PCT/US2019/021643 dated May 30, 2019.
International Search Report of the ISA for priority application PCT/US2019/021643 dated May 30, 2019.

* cited by examiner

*Primary Examiner* — Ganapathirama Raghu
(74) *Attorney, Agent, or Firm* — Eva Leah Taksel

(57) ABSTRACT

Aqueous fermentation feedstock and method of producing same. The feedstock includes glucose and dextrose oligomers, wherein (i) glucose concentration is in a range between 10 gram/Liter (g/L) and 150 g/L; (ii) dextrose oligomers concentration is in a range between 50 g/L and 300 g/L; and optionally (iii) slurried particles of less than 0.5 micron; (iv) slurried particles of more than 0.5 micron, wherein a content of such suspended particles of more than 0.5 micron is less than 30 g/L; (v) ash at a concentration in a range between 20 g/L and 50 g/L; (vi) lactate at a concentration in a range between 0.5 g/L and 10 g/L; (vii) protein at a concentration in a range between 5 g/L and 50 g/L; (viii) corn oil at a concentration of less than 10 g/L; and/or (ix) glycerol at a concentration in a range between 1 g/L and 30 g/L.

9 Claims, No Drawings

AQUEOUS FERMENTATION FEEDSTOCK AND A METHOD FOR THE PRODUCTION THEREOF

BACKGROUND OF THE INVENTION

The cost of fermentation feedstock is a major contributor to the cost of fermentation products. There is, therefore, a strong need for low cost fermentation feedstock and for methods of producing thereof.

SUMMARY OF THE INVENTION

According to an embodiment, provided is an aqueous fermentation feedstock comprising glucose and dextrose oligomers, wherein (i) glucose concentration is in the range between 10 gram/Liter (g/L) and 150 g/L; (ii) dextrose oligomers concentration is in the range between 50 g/L and 300 g/L; and optionally (iii) slurried particles of less than 0.5 micron; (iv) slurried particles of more than 0.5 micron, wherein the content of such suspended particles of more than 0.5 micron is less than 30 g/L; (v) ash at a concentration in the range between 20 g/L and 50 g/L; (vi) lactate at a concentration in the range between 0.5 g/L and 10 g/L; (vii) protein at a concentration in the range between 5 g/L and 50 g/L; (viii) corn oil at a concentration of less than 10 g/L; and/or (ix) glycerol at a concentration in the range between 1 g/L and 30 g/L. According to an embodiment, provided is an aqueous fermentation feedstock is characterized by being sterile.

According to an embodiment, provided is a method for producing said aqueous fermentation feedstock, comprising (i) providing corn kernels; (ii) comminuting said corn kernels to form comminuted corn kernels; (iii) forming an aqueous slurry of said comminuted corn kernels; (iv) treating said slurry with alpha-amylase enzymes and optionally also with gluco-amylase, at a temperature greater than 150 degrees Fahrenheit, whereby a corn mash is formed, wherein said corn mash comprises water soluble carbohydrates and water-insoluble carbohydrates; (v) filtering at least a fraction of said corn mash as a filtration feed on a microfiltration membrane; whereby an aqueous filtration permeate, comprising said water-soluble carbohydrates, and a filtration retentate comprising said water-insoluble carbohydrates, are formed; and (vi) separating said filtration permeate from said filtration retentate, to form separated permeate and separated retentate.

According to an embodiment, the duration of said treating with alpha-amylase enzymes is in the range between 30 minutes and 300 minutes. According to an embodiment, said treating further comprises grinding of said slurry. According to an embodiment, said treating further comprises jet-cooking of said slurry.

According to an embodiment, said microfiltration membrane is selected from the group consisting of sintered stainless steel membranes, polymeric membranes and ceramic membranes. According to an embodiment, said microfiltration membrane is sintered stainless steel membrane with ceramic coating. According to an embodiment, said ceramic coating comprises titanium oxide. According to an embodiment, said microfiltration membrane is characterized by porosity in the range between 0.01 micron and 0.5 micron.

According to an embodiment, said filtering is characterized by at least one of (i) feed, permeate and retentate temperature ranging between 100 and 210 degrees Fahrenheit; (ii) feed pressure ranging between 2 and 10 atmospheres gauge; (iii) retentate pressure ranging between 2 and 10 atmospheres gauge; (iv) permeate pressure ranging between 1 and 8 atmospheres gauge; (v) circulation or feed flow rate that creates a linear velocity within the membranes of at least 5 feet per second; and (vi) transmembrane pressure drop ranging between 1 and 10 atmospheres gauge.

According to an embodiment, provided is a method for the production of single-cell protein, comprising culturing selected organisms in said aqueous fermentation feedstock. According to another embodiment, provided is an integrated method for the production of single-cell protein and ethanol, comprising fermenting said water-soluble carbohydrates in said separated permeate to form single cell protein and fermenting said water-insoluble carbohydrate in said separated retentate to form ethanol.

DETAILED DESCRIPTION OF THE INVENTION

The particulars shown herein are by way of example and for purposes of illustrative discussion of the various embodiments of the present invention only and are presented in the cause of providing what is believed to be the most useful and readily understood description of the principles and conceptual aspects of the invention. In this regard, no attempt is made to show details of the invention in more detail than is necessary for a fundamental understanding of the invention, the description making apparent to those skilled in the art how the several forms of the invention may be embodied in practice.

The present invention will now be described by reference to more detailed embodiments. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

Additional advantages of the invention will be set forth in part in the description, which follows, and in part will be obvious from the description, or may be learned by practice of the invention. It is to be understood that both the foregoing general description and the following detailed description are exemplary and explanatory only and are not restrictive of the invention, as claimed.

According to an embodiment, provided is an aqueous fermentation feedstock comprising glucose and dextrose oligomers, wherein (i) glucose concentration is in the range between 10 gram/Liter (g/L) and 150 g/L; (ii) dextrose oligomers concentration is in the range between 50 g/L and 300 g/L; and optionally (iii) slurried particles of less than 0.5 micron; (iv) slurried particles of more than 0.5 micron, wherein the content of such suspended particles of more than 0.5 micron is less than 30 g/L; (v) ash at a concentration in the range between 20 g/L and 50 g/L; (vi) lactate at a concentration in the range between 0.5 g/L and 10 g/L; (vii) protein at a concentration in the range between 5 g/L and 50 g/L; (viii) corn oil at a concentration of less than 10 g/L; and/or (ix) glycerol at a concentration in the range between 1 g/L and 30 g/L.

As used herein, the term dextrose oligomers refers to oligomers of various degrees of polymerization (DP), e.g. $DP_2$, $DP_3$, $DP_4$ and higher degrees of polymerization, e.g. $DP_{10}$.

According to an embodiment, glucose concentration in said fermentation feedstock is in the range between 10 gram/Liter (g/L) and 150 g/L, between 30 g/L and 130 g/L or between 60 g/L and 120 g/L. According to an embodiment, the concentration of the dextrose oligomers in said fermentation feedstock is in the range between 50 g/L and 300 g/L, between 60 g/L and 200 g/L, between 70 g/L and 180 g/L or between 80 g/L and 150 g/L.

According to an embodiment, said fermentation feedstock is clear. According to an embodiment, said fermentation feedstock comprises slurried particles, e.g. slurried starch particles. According to an embodiment, said particles are of less than 0.5 micron. According to an embodiment, said particles are of more than 0.5 micron, and the content of such suspended particles of more than 0.5 micron is less than 30 g/L, less than 20 g/L or less than 10 g/L.

According to an embodiment, said fermentation feedstock comprises ash, lactate, protein, corn oil and/or glycerol. According to an embodiment ash concentration is in the range between 20 g/L and 50 g/L, or between 30 g/L and 40 g/L. According to an embodiment, lactate concentration is in the range between 0.5 g/L and 10 g/L, between 1 g/L and 8 g/L or between 2 g/L and 6 g/L.; (vii) According to an embodiment, protein concentration is in the range between 5 g/L and 50 g/L, between 10 g/L and 40 g/L or between 20 g/L and 30 g/L. According to an embodiment, corn oil concentration is less than 10 g/L, less than 8 g/L or less than 6 g/L. According to an embodiment, glycerol concentration is in the range between 1 g/L and 30 g/L, between 2 g/L and 25 g/L or between 3 g/L and 20 g/L.

According to an embodiment, said aqueous fermentation feedstock is characterized by being sterile. According to an embodiment, said aqueous fermentation feedstock is characterized by a specific gravity greater than 1.05. According to an embodiment, said aqueous fermentation feedstock is characterized by yellow to brown color.

According to an embodiment, provided is a method for producing said aqueous fermentation feedstock, comprising (i) providing corn kernels; (ii) comminuting said corn kernels to form comminuted corn kernels; (iii) forming an aqueous slurry of said comminuted corn kernels; (iv) treating said slurry with alpha-amylase enzymes and optionally also with gluco-amylase, at a temperature greater than 150 degrees Fahrenheit, whereby a corn mash is formed, wherein said corn mash comprises water soluble carbohydrates and water-insoluble carbohydrates; (v) filtering at least a fraction of said corn mash as a filtration feed on a microfiltration membrane; whereby an aqueous filtration permeate, comprising said water-soluble carbohydrates, and a filtration retentate comprising said water-insoluble carbohydrates, are formed; and (vi) separating said filtration permeate from said filtration retentate, to form separated permeate and separated retentate.

According to an embodiment, said providing corn kernels, said comminuting corn kernels, said forming an aqueous slurry and/or said treating the slurry with alpha-amylase enzymes are conducted using apparatus and conditions similar to those used in corn dry milling. According to an embodiment, said forming a slurry comprises using water and/or aqueous solutions generated in corn dry milling ethanol production. According to an embodiment, said forming a slurry comprises using water and/or aqueous solutions generated in corn dry milling ethanol production comprises ethanol stripped fermentation broth and/or ethanol plant evaporator condensate.

According to an embodiment, said treating with enzymes is conducted at a temperature greater than 160 degrees Fahrenheit, greater than 170, greater than 180 or about 185 degrees Fahrenheit. According to an embodiment, the duration of said treating with alpha-amylase enzymes is in the range between 30 minutes (min.) and 300 min, between 60 min and 240 min or between 90 min and 160 min.

According to an embodiment, said treating comprises at least one of grinding said slurry and jet-cooking of said slurry. According to an embodiment, said grinding and/or jet-cooking is conducted using apparatus and conditions similar to those used in corn dry milling. According to an embodiment, said treating comprises additionally treating said slurry with gluco-amylase. According to an embodiment, said additionally treating said slurry with gluco-amylase is conducted at a temperature between 100 and 150 degrees Fahrenheit.

According to an embodiment, said method comprises filtering at least a fraction of said corn mash on a microfiltration membrane. According to an embodiment, said filtering comprises feeding said corn mash to a microfiltration unit comprising at least one microfiltration membrane. Said fed corn mash, comprising water-soluble carbohydrates and water-insoluble carbohydrates, is also referred to as filtration feed. According to an embodiment, said filtering generates an aqueous filtration permeate, comprising said water-soluble carbohydrates, and a filtration retentate comprising said water-insoluble carbohydrates. According to an embodiment, said method comprises separating said filtration permeate from said filtration retentate, to form separated permeate and separated retentate. Any form of separating is suitable.

According to an embodiment, feed flow rates is in the range between 0.3 and 1.2 gallon per minute per square feet of the membrane. According to an embodiment, permeate flow rates to is in the range between 0.01 and 0.1 gallon per minute per square feet of the membrane.

According to an embodiment, said filtering is characterized by at least one of feed, permeate and retentate temperature ranging between 100 and 210 degrees Fahrenheit, between 120 and 180 or between 130 and 160 degrees Fahrenheit. According to an embodiment, said filtering is characterized by feed pressure ranging between 2 and 10 atmospheres gauge, between 3 and 8 or between 4 and 6 atmospheres gauge. According to an embodiment, said filtering is characterized by retentate pressure ranging between 2 and 10 atmospheres gauge, between 3 and 8 or between 4 and 6 atmospheres gauge. According to an embodiment, said filtering is characterized by permeate pressure ranging between 1 and 8 atmospheres gauge, between 2 and 7 or between 3 and 6 atmospheres gauge. According to an embodiment, said filtering is characterized by transmembrane pressure drop ranging between 1 and 10 atmospheres gauge, between 2 and 9 or between 3 and 8 atmospheres gauge. According to an embodiment, said filtering comprises circulation or feed flow rate that creates a linear velocity within the membranes of at least 5 feet per second.

According to an embodiment, said microfiltration membrane is selected from the group consisting of sintered stainless steel membranes, polymeric membranes and ceramic membranes. According to an embodiment, said polymeric membranes is in hollow-fiber, in spiral wound and/or in plate and frame form, According to an embodiment, said microfiltration membrane is a sintered stainless steel membrane with ceramic coating. According to an embodiment, said ceramic coating comprises titanium oxide. According to an embodiment, said microfiltration membrane is characterized by porosity in the range between 0.01 micron and 0.5 micron, between 0.01 micron and 0.4 micron, between 0.01 micron and 0.3 micron, between 0.02 micron and 0.2 micron or about 0.1 micron.

According to an embodiment, provided is a method for the production of single-cell protein, comprising culturing selected organisms in said aqueous fermentation feedstock. According to an embodiment, said culturing comprises metabolizing at least a fraction of said soluble carbohydrate and optionally also at least a fraction of said glycerol and/or said lactate. According to an embodiment, said culturing is conducted in at least one mode selected from the group consisting of batch, batch simultaneous saccharification and fermentation (SSF), fed batch, fed batch SSF, continuous and continuous SSF.

According to an embodiment, said method further comprises separating at least a fraction of said single-cell protein. According to an embodiment, provided is a protein feed ingredient comprising said single-cell protein. According to an embodiment, provided is a protein feed ingredient comprising said single-cell protein and at least a fraction of the protein in said fermentation feedstock.

According to an embodiment, provided is a method for the production of single-cell protein and ethanol, comprising fermenting said water-soluble carbohydrates in said separated permeate to form single cell protein and fermenting said water-insoluble carbohydrate in said separated retentate to form ethanol. According to an embodiment, the method comprises sending said retentate to a mash cooler/beer preheater heat exchanger and then to ethanol fermentation. According to an embodiment, the method comprises sending said retentate to a mash cooler heat exchanger and then to a bio-catalytic or thermo-mechanical conversion or to a drying or to a subsequent mechanical fractionation process.

EXAMPLE

This example illustrates the generation of an aqueous fermentation feed and subsequent fermentation to generate a single-cell protein. To prepare the aqueous fermentation feed, a corn mash was first prepared. The corn mash was made by grinding corn in a hammermill to about 1 mm in diameter, mixing the ground corn with water into a slurry until a total solids percentage of 36% (g/g) is achieved, adding an alpha-amylase to the slurry, and then cooking the slurry at 87-88° C. The corn mash was then diluted by half to a total solids percentage of about 18% (g/g) and fed into a microfiltration skid. The microfiltration skid was made up of Spector® membranes, $TiO_2$-coated sintered stainless steel membranes, manufactured by Graver Technologies with a pore size of 0.1 micron. The system was run at 2.4 atm and 65° C. The permeate, consisting of soluble dextrose oligomers, glucose monomers, and water, was sent to the fermentation vessel, while the retentate was washed twice with water. The washes were also sent to the fermentation vessel. The final aqueous feed in the fermentation vessel was about 30 g/L glucose monomers and 60-70 g/L dextrose oligomers.

A trace vitamin solution and a mineral solution were added to the fermentation at 10 mL per L of volume each. The vitamin solution consisted of 2 mg/L biotin, 2 mg/L folic acid, 10 mg/L pyridoxine-HCl, 5 mg/L thiamine-HCl, 5 mg/L riboflavin, 5 mg/L nicotinic acid, 5 mg/L calcium D-(+)-pantothenate, 0.1 mg/L vitamin B12, 5 mg/L p-aminobenzoic acid, and 5 mg/L thioctic acid, and the mineral solution consisted of 2 g/L nitrilotriacetic acid, 1 g/L $MnSO_4.H_2O$, 0.8 g/L $Fe(SO_4)_2(NH_4)_2.6H_2O$, 0.2 g/L $CoCl_2.6H_2O$, 0.2 mg/L $ZnSO_4.6H_2O$, 0.02 g/L $CuCl_2.2H_2O$, 0.02 g/L $NiCl_2.6H_2O$, 0.02 g/L $Na_2MoO_4.2H_2O$, 0.02 g/L $Na_2SeO_4$, and 0.02 g/L $Na_2WO_4$. The fermenter was inoculated with a single cell protein strain, *Clostridium tyrobutyricum*, and the fermenter was operated at 35° C. and pH 6.0, with a 6M ammonium hydroxide base solution used for maintaining the pH. After about 16 hours, the fermentation was exhausted, and the cell mass was collected and dried into a single cell protein product.

The invention claimed is:

1. An aqueous bacterial fermentation feedstock comprising glucose and dextrose oligomers, wherein
   (i) glucose concentration is in the range between 10 gram/Liter (g/L) and 150 g/L;
   (ii) dextrose oligomers concentration is in the range between 50 g/L and 300 g/L; and
   (iii) less than 30 g/L of slurried starch particles having a size of more than 0.5 micron; and
   at least one selected from the group consisting of:
   (iv) slurried starch particles of less than 0.5 micron;
   (v) ash at a concentration in the range between 20 g/L and 50 g/L;
   (vi) lactate at a concentration in the range between 0.5 g/L and 10 g/L;
   (vii) protein at a concentration in the range between 5 g/L and 50 g/L;
   (viii) corn oil at a concentration of less than 10 g/L; and
   (viii) glycerol at a concentration in the range between 1 g/L and 30 g/L.

2. The aqueous bacterial fermentation feedstock of claim 1, characterized by being sterile.

3. A method for producing said aqueous bacterial fermentation feedstock of claim 1, comprising
   (i) providing corn kernels;
   (ii) comminuting said corn kernels to form comminuted corn kernels;
   (iii) forming an aqueous slurry of said comminuted corn kernels;
   (iv) treating said slurry with alpha-amylase enzymes and optionally also with gluco-amylase, at a temperature greater than 150 degrees Fahrenheit, whereby a corn mash is formed, wherein said corn mash comprises water soluble carbohydrates and water-insoluble carbohydrates;

(v) filtering at least a fraction of said corn mash as a filtration feed on a microfiltration membrane comprising sintered stainless steel with a ceramic coating comprising titanium dioxide, wherein said filtering is characterized by at least one of:
 (a) feed, permeate and retentate temperature ranging between 100 and 210 degrees Fahrenheit;
 (b) feed pressure ranging between 2 and 10 atmospheres gauge;
 (c) retentate pressure ranging between 2 and 10 atmospheres gauge;
 (d) permeate pressure ranging between 1 and 8 atmospheres gauge;
 (e) circulation or feed flow rate that creates a linear velocity within the membranes of at least 5 feet per second; and
 (f) transmembrane pressure drop ranging between 1 and 10 atmospheres gauge;
whereby an aqueous filtration permeate, comprising said water-soluble carbohydrates, and a filtration retentate comprising said water-insoluble carbohydrates, are formed; and (vi) separating said filtration permeate from said filtration retentate, to form separated permeate and separated retentate.

4. The method of claim 3, wherein the duration of said treating with alpha-amylase enzymes is in the range between 30 minutes and 30 minutes.

5. The method of claim 3, wherein said treating further comprises grinding of said slurry.

6. The method of claim 3, wherein said treating further comprises jet-cooking of said slurry.

7. The method of claim 3, wherein said microfiltration membrane is characterized by porosity in the range between 0.01 micron and 0.5 micron.

8. A method for the production of bacterial single-cell protein, comprising culturing selected bacteria in an aqueous fermentation feedstock according to claim 1.

9. An integrated method for the production of bacterial single-cell protein and ethanol, comprising fermenting said water-soluble carbohydrates in said separated permeate of claim 3 to form bacterial single cell protein and fermenting said water-insoluble carbohydrate in said separated retentate of claim 3 to form ethanol.

* * * * *